United States Patent
Bishop

[19]

[11] Patent Number: 6,091,488
[45] Date of Patent: Jul. 18, 2000

[54] METHOD OF AND APPARATUS FOR AUTOMATIC HIGH-SPEED OPTICAL INSPECTION OF SEMI-CONDUCTOR STRUCTURES AND THE LIKE THROUGH FLUORESCENT PHOTORESIST INSPECTION

[75] Inventor: Robert Bishop, Newton, Mass.

[73] Assignee: Beltronics, Inc.

[21] Appl. No.: 09/275,349

[22] Filed: Mar. 22, 1999

[51] Int. Cl.$^7$ .................................................. G01N 21/00
[52] U.S. Cl. ........................................................ 356/237.5
[58] Field of Search ............................. 356/237.2, 237.3, 356/237.4, 237.5

[56] References Cited

U.S. PATENT DOCUMENTS 5,278,012  1/1994  Yamanaka et al. ................. 356/237.5
5,951,837  9/1999  Craig et al. ......................... 356/237.5

*Primary Examiner*—Frank G. Font
*Assistant Examiner*—Zandra V. Smith
*Attorney, Agent, or Firm*—Rines and Rines

[57] ABSTRACT

Semiconductor wafers, circuit boards and similar multi-layer structures are optically inspected at high speeds with the aid of preferably a pair of oppositely and inclinedly directed laser beams at inclined angles to the vertical and the wafer surface to cause fluorescence by a photoresist layer carrying conductor patterns, defects in which are to be inspected, and using preferably a time-delay-integration CCD imaging camera for recording a fluorescent resist surface image accentuating the non-fluorescing conductor pattern thereupon, while masking all light from layers therebelow.

20 Claims, 15 Drawing Sheets

METHOD OF AND APPARATUS FOR AUTOMATIC HIGH-SPEED OPTICAL INSPECTION OF SEMI-CONDUCTOR STRUCTURES AND THE LIKE THROUGH FLUORESCENT PHOTORESIST INSPECTION

The present invention relates to the optical inspection of semi-conductor structures and the like, such as multi-layer wafers, chips, circuit boards, etc., being more specifically, though not exclusively, concerned with high speed inspection for defects or artifacts and the like, and to the employment therein of selective layer fluorescence as an aid to preferential discriminative or selective imaging of predetermined surfaces or layers or parts of such structures.

BACKGROUND

The use of a laser-beam-excited fluorescing top dielectric layer of a multi-layered semi-conductor wafer or chip or the like for the purpose of shadowing conductor patterns deposited on controlled flat surfaces thereof, and thereby masking layers therebelow, is described in U.S. Pat. No. 5,278,012 to Yamanaka et al; and improvements thereupon for enabling the use of such techniques with rough or randomly bumpy layers or surfaces and protruding angle conductors is accomplished by the techniques described in my co-pending U.S. patent application Ser. No. 08/880,836, filed Jun. 23, 1997, for "Method Of Optically Inspecting Multi-Layered Electronic Parts And The Like With Fluorescent Scattering Top-Layer Discrimination And Apparatus Therefor".

The use of fluorescence in inspection systems for other purposes has also been taught, as, for example, fluorescing epoxy circuit boards to enable ignoring grainy metallic conductors in structures having high contrast in the visible spectrum (equipment of Orbot Company and others), but not addressing the problem of eliminating images from lower layers. It has further been proposed (Hughes Company) to use television cameras to enable an operator to view, in one large field, the fluorescence of the corner only of wafers located in a cassette, to determine whether resist has been applied or removed from each wafer as a means of process control, as described in the article "High Throughput Inspection Tool For Photoresist Patterning", Semiconductor International, September, 1997.

The present invention, on the other hand, addresses the very much more rigorous and difficult problem of automatically performing a one hundred percent high speed scanning inspection of the complete surface of every wafer for all defects in the resist patterns thereof, such as hairline shorts, pinholes, incorrect line width or spacing or morphology, and for other defects in the patterned resist. The invention, moreover, does so through a novel technique for photoresist fluorescence and automatic image analysis of the whole wafer surface, including defects that, unlike in the television large field-of-view corner inspection of the said article, may represent only a small fraction of the viewed image. As an example, the invention enables a pin hole defect of but one or two pixels to be detected, which would not be detectable in large bright fields of fluorescing resist as in the technique of said article. The invention additionally permits of automatic analysis of the wafer pattern as to its conformity to design rules, known good reference images, and adjacent circuit patterns on the wafer or the like for checking correct pattern morphology, as well.

OBJECTS OF INVENTION

It is accordingly an object of the present invention to provide a new and improved method of and apparatus for enabling the high speed optical scanning inspection of multi-layer wafers, chips and other semi-conductors and similar devices, that shall not be subject to the prior art limitations above discussed; but that, to the contrary, shall enable the automatic total inspection for defects and defect-free deposition of photoresists in the fabrication process of each wafer layer, accurately defining the location of the desired conductors and other circuit structures thereon and their absence.

A further object is to provide such a novel technique that enables the automatic or semi-automatic inspection of resist patterns to verify correct pattern geometry, and to detect defects such as opens, shorts, nicks, protrusions, etc. and also residual unremoved or undeveloped resist scum and the like which, in metal subtractive processes, later described, can prevent proper removal of metal during acid etch that can cause shorts and protrusion type defects; and, in metal additive processes, as later more fully explained, can prevent a second layer of heavier metal from being deposited or chemically bonding to base metal below the scum, causing voids or breaks.

An additional object is to provide for such inspection when the photoresist has been deposited on metal layers and before etching of the underlying metal, to enable repair in the resist application stage of fabrication before etching.

Still a further object is to provide a new and improved laser-induced fluorescing photoresist inspection system of more general utility, as well.

Other and further objects will be explained hereinafter and are more fully pointed out in the appended claims.

SUMMARY

In summary, from one of its important instrumentation aspects, the invention embraces apparatus for optically inspecting the light-opaque conductor line pattern on the top layer of a multi-layer integrated circuit wafer and the like to the exclusion of patterns on lower layers, wherein the conductor line pattern is formed on such a top layer of a material that fluoresces in response to laser light of predetermined frequency(ies) and wherein the fluorescing frequency is different from the predetermined frequency, said apparatus having, in combination, means for generating and directing laser light of said predetermined frequency(ies) upon said top layer along a pair of beams impinged from opposite sides of the layer at opposite inclined angles thereto; means for optically inspecting the light of said different frequency fluorescing from the top layer in response to directing of the pair of beams thereupon, creating an illuminated top layer fluorescing light background masking the lower layers and upon which the conductor line pattern appears as dark lines; means for adjusting the operation of the pair of laser beams to avoid exact frequency coherency that might generate frequency beats; and means for adjusting said opposite inclined angles of the pair of beams to eliminate the generation of dark shadow zones between proximal edges of adjacent conductor lines between the lines that might otherwise be misinterpreted as a dark conductor line.

From a broader viewpoint, the invention also encompasses a method of optically inspecting the light-opaque conductor line pattern on the top layer of a multi-layer integrated circuit wafer and the like to the exclusion of patterns on lower layers, that comprises, forming the conductor line pattern on such a top layer of a material that fluoresces in response to laser light of predetermined frequency(ies) and wherein the fluorescing frequency is different from the predetermined frequency-directing laser light of said predetermined frequency(ies) upon said layer at an inclined angle thereto; optically inspecting the light of said different frequency fluorescing from the top layer in response to directing of the laser light thereupon, creating an illuminated top layer fluorescing light background masking the lower layers and upon which background the conductor line pattern appears as dark lines; and adjusting said inclined angle to minimize the generation of dark shadow zones between proximal edges of adjacent conductor lines between the lines that might otherwise be misinterpreted as a dark conductor line.

Preferred and best mode designs and details are hereinafter described in detail.

DRAWINGS

The invention will now be described with reference to the accompanying drawings wherein FIG. 1A is a white light-reflected image of a multi-layered semiconductor wafer having a photoresist-metal conductor pattern uneven surface;

Figure 6:
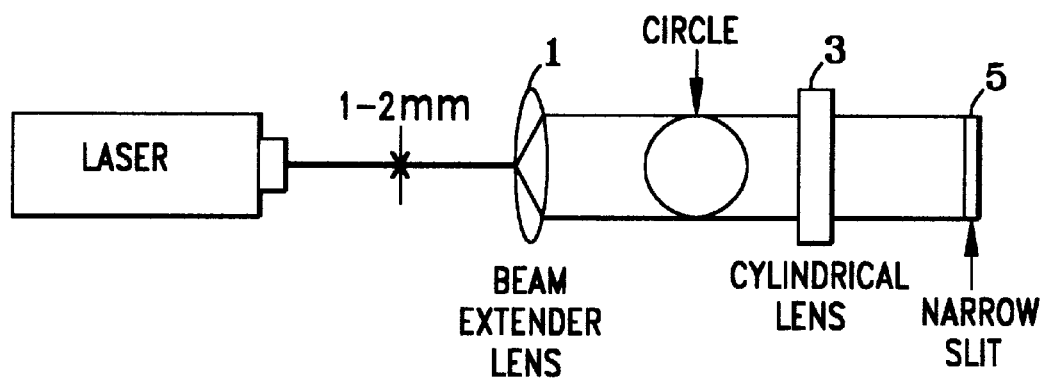
Figure 7:
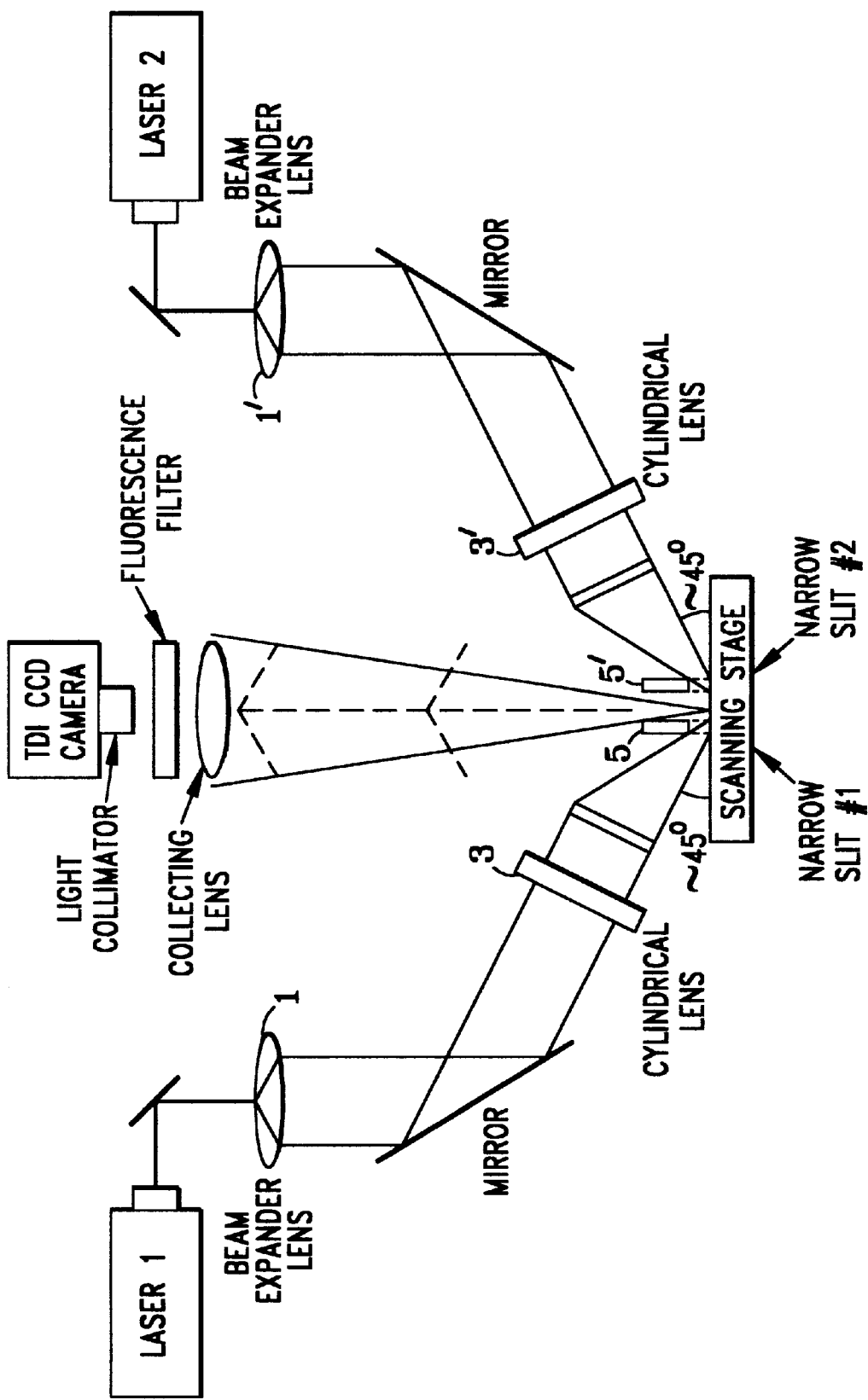
Figure 7A:
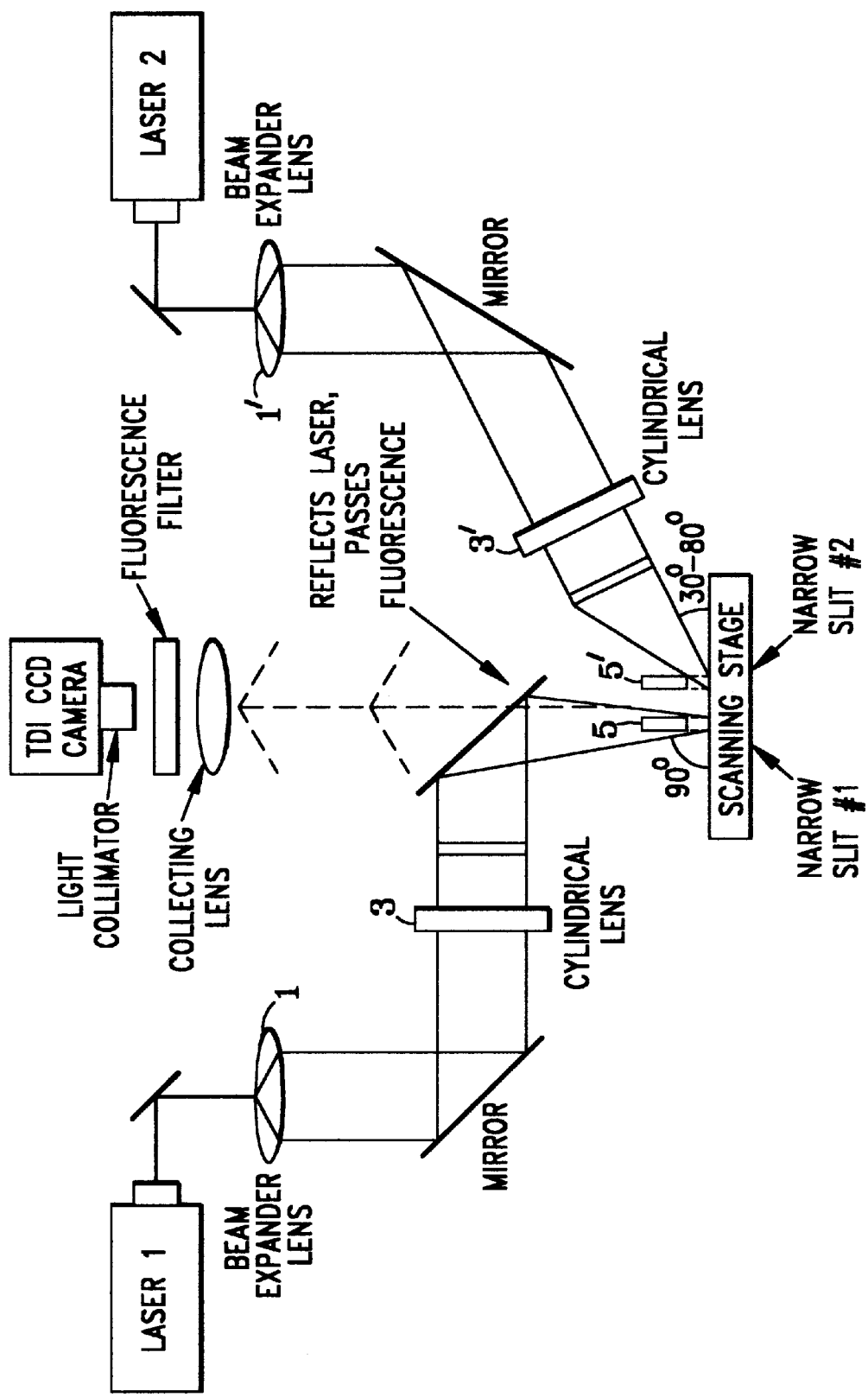
Figure 8:
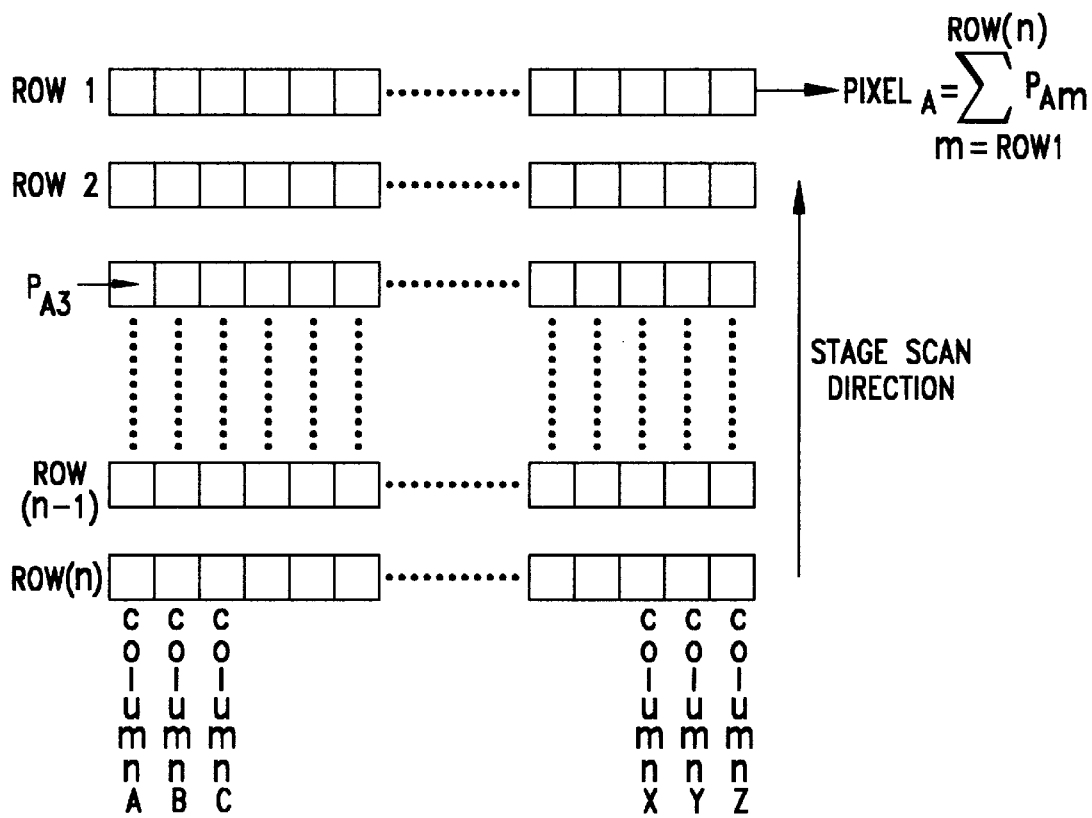
Figure 9:
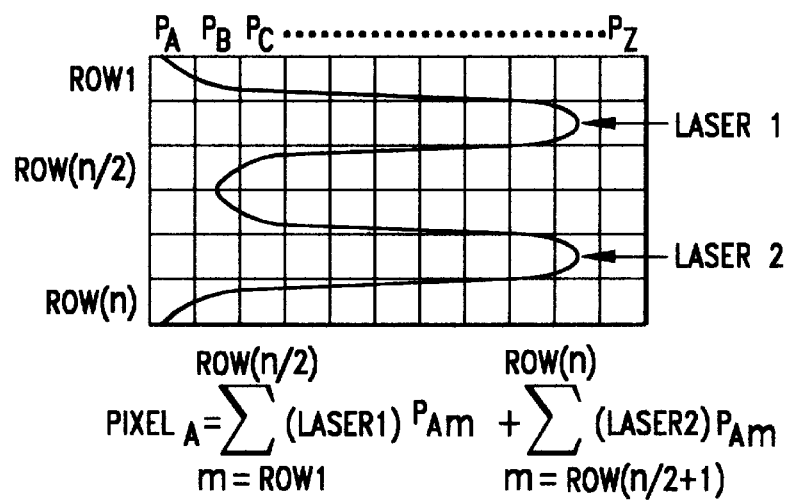
Figure 10:
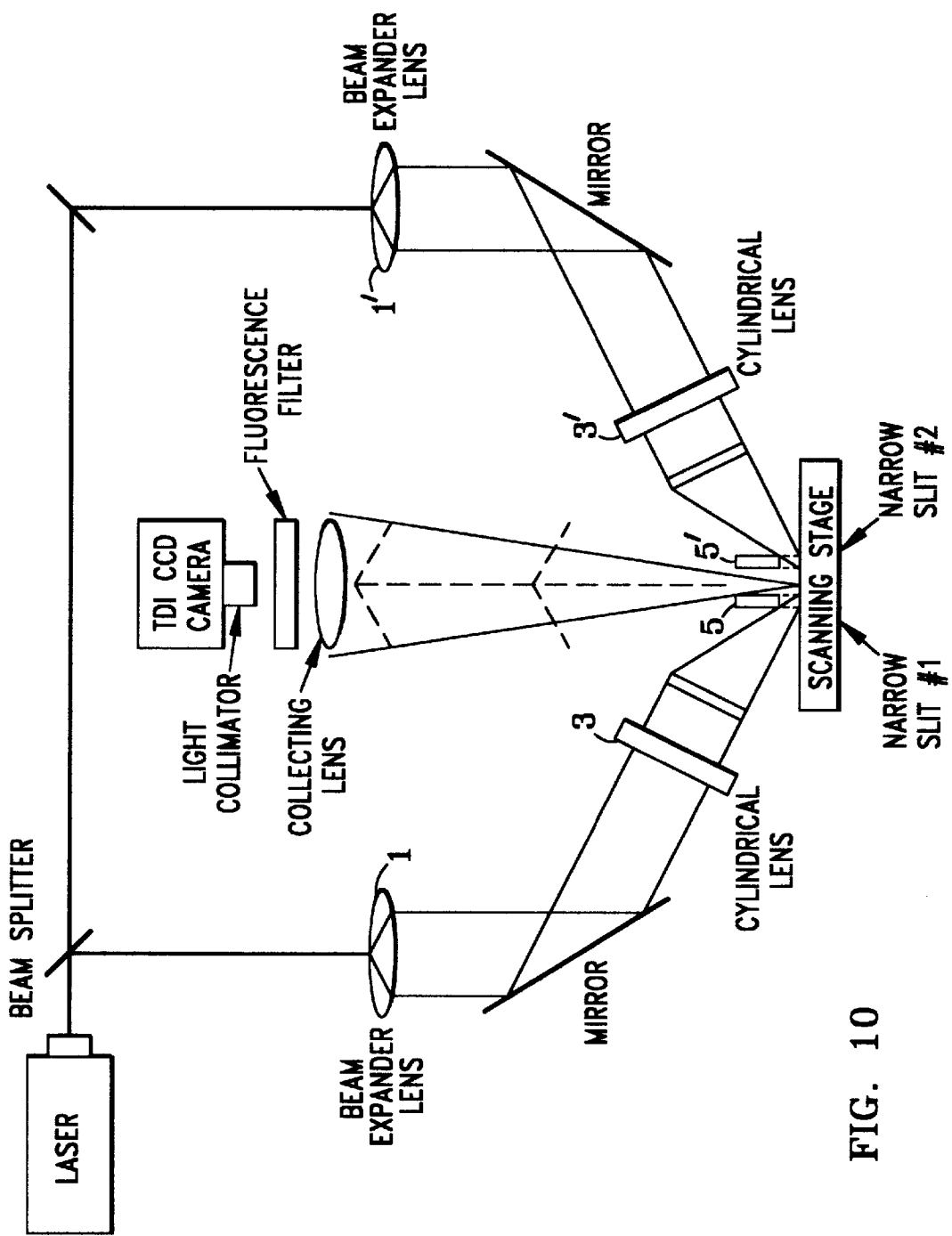
Figure 11:
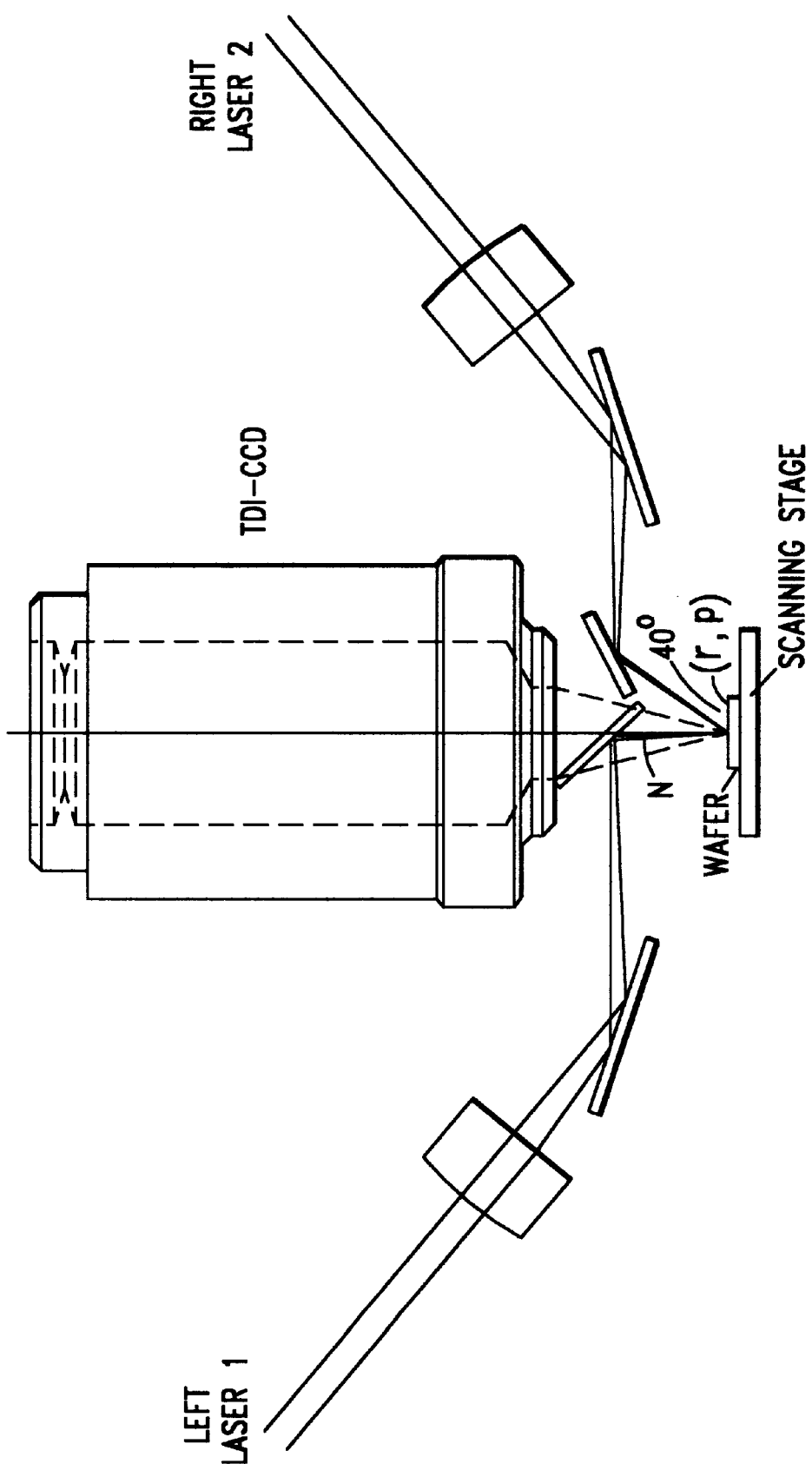
Figure 12:
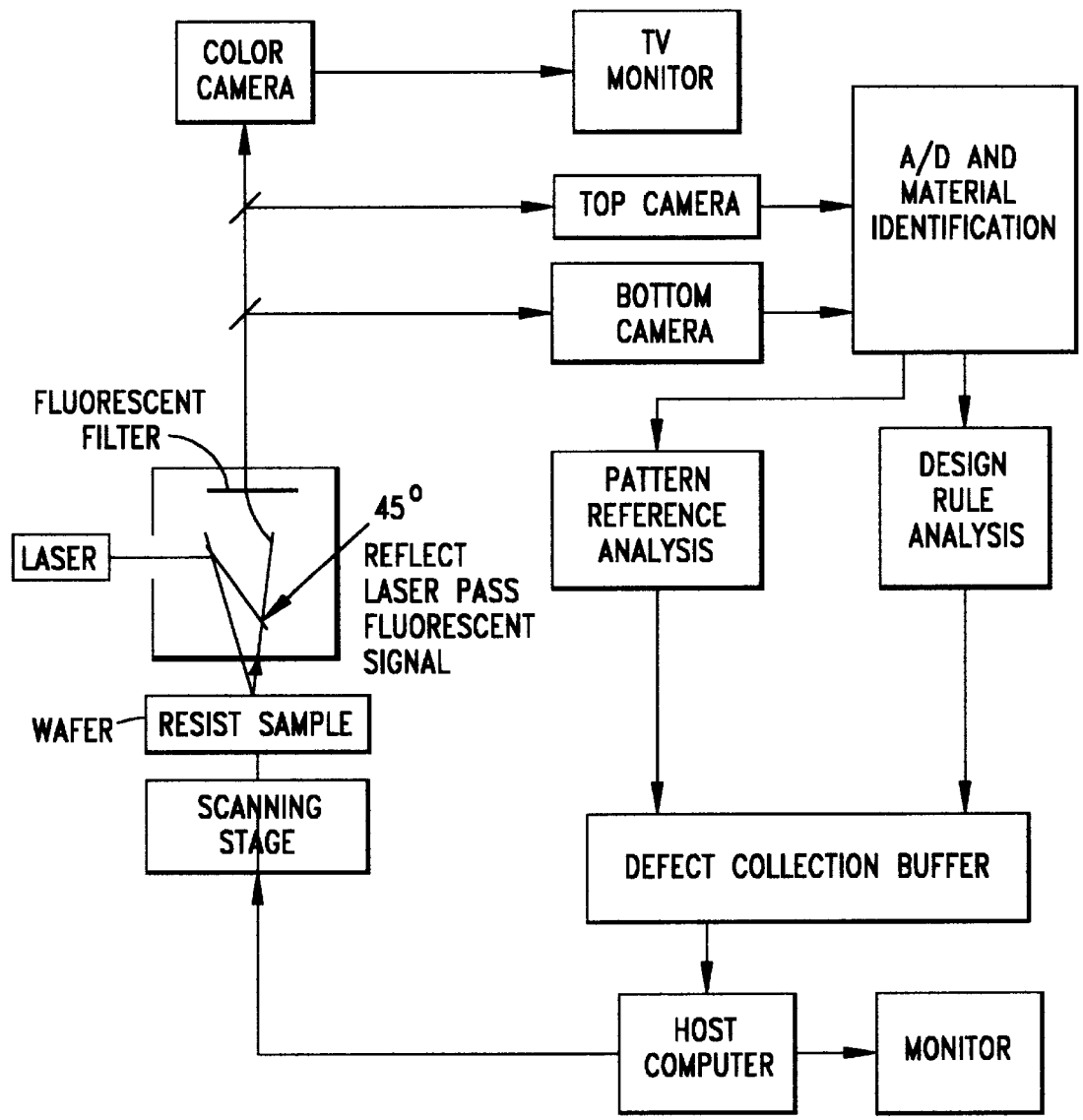

FIGS. 3(a)–(e) are schematic longitudinal sections of successive steps in the manufacture of the wafer by a positive resist additive process;

FIGS. 4(a)–(e) are similar steps for a negative resist subtractive process;

FIGS. 5(a)–(e) are similar steps for a positive resist with additive and subtractive processes;

FIG. 6 is an optical laser beam slit forming diagram;

FIG. 7 is a schematic optical path diagram for a preferred optical inspection apparatus using a pair of oppositely directed fluorescence-exciting laser beams directed inclinedly upon the wafer surface;

FIG. 8 and 9 are diagrams of the TDI-CCD pixel sensor array;

FIG. 10 is a view similar to FIG. 7 of a modification;

FIG. 11 is also a view similar to FIG. 7, but in more structural and less diagrammatic form, of another modification; and FIG. 12 is a block diagram of an automatic inspection system

PREFERRED EMBODIMENT(S) OF THE INVENTION

Before preceding to describe preferred apparatus for implementing the novel inspection method or technique underlying the present invention, it is believed useful and important first to review how semi-conductor structures are fabricated, and the possible defects in photoresist-conductor pattern etching on developing that it is important to detect by automatic or machine optical inspection.

Introduction

As before explained, semiconductor wafers and the like consist of one or more layers of conducting (metal) material. Fabrication of each layer requires the deposition of photoresist to define where the circuit structures are to be placed.

Fluorescence, as also previously explained, can be used to inspect the photoresist pattern. When the photoresist is deposited on metal, this invention enables the resist pattern to be inspected before etching the metal beneath. One can repair a defect in the resist stage; but it is much more difficult, perhaps impossible, to do so after etching.

Figure 1A:
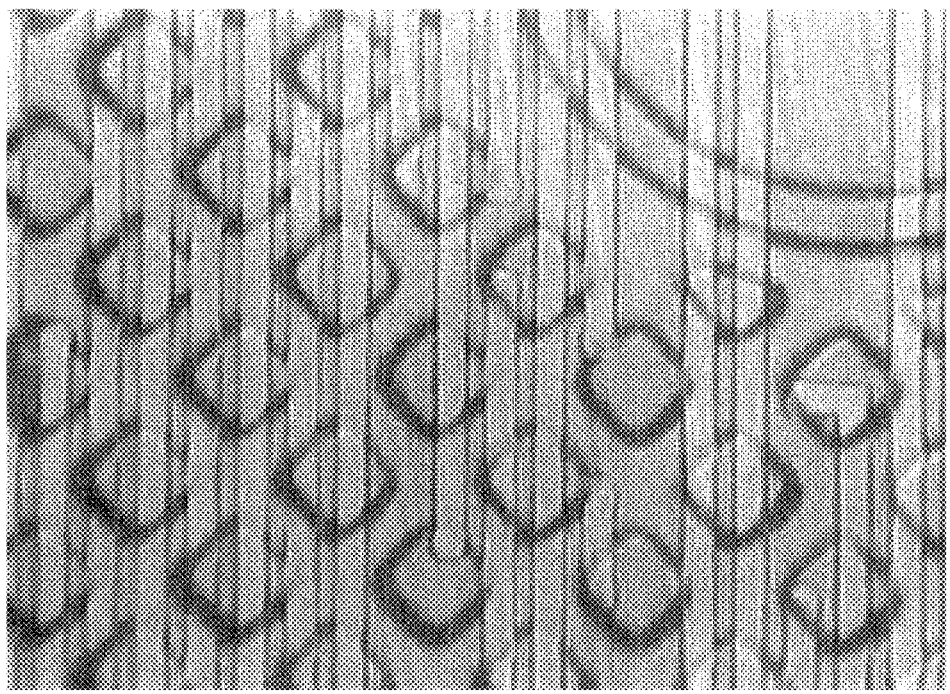
FIG. 1B is a fluorescent light image of the same wafer produced in accordance with the method and apparatus of the invention, showing the effective masking bright background of fluorescing resist that accentuates the conductor pattern to be inspected as dark shadow lines.
Figure 2A:
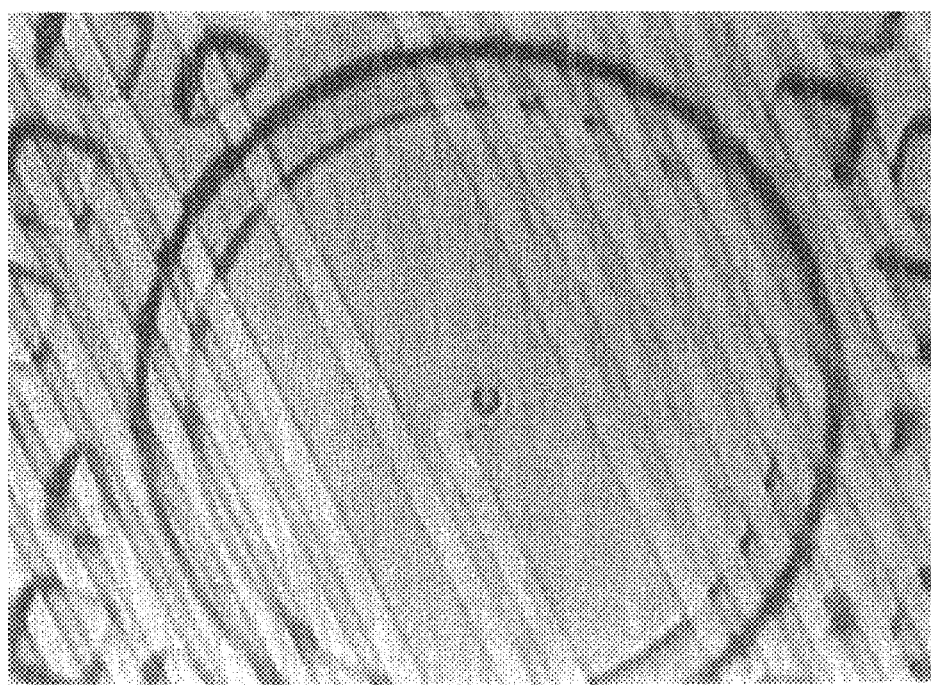
FIGS. 2A and 2B are similar respectively to FIGS 1A and 1B of via hole regions of such wafers.

Both positive and negative resists used to manufacture semiconductors can be made to fluoresce, rendering invisible the surface beneath, in the manner described in my copending application for dielectric top layers. Such lower surfaces may often have an uneven topology that produces dark patterns in the visible white light image, as shown in FIGS. 1A and 2A. FIGS. 1A and 2A show optical images of a photoresist on uneven metal conductor surfaces under white light.

Figure 1B:
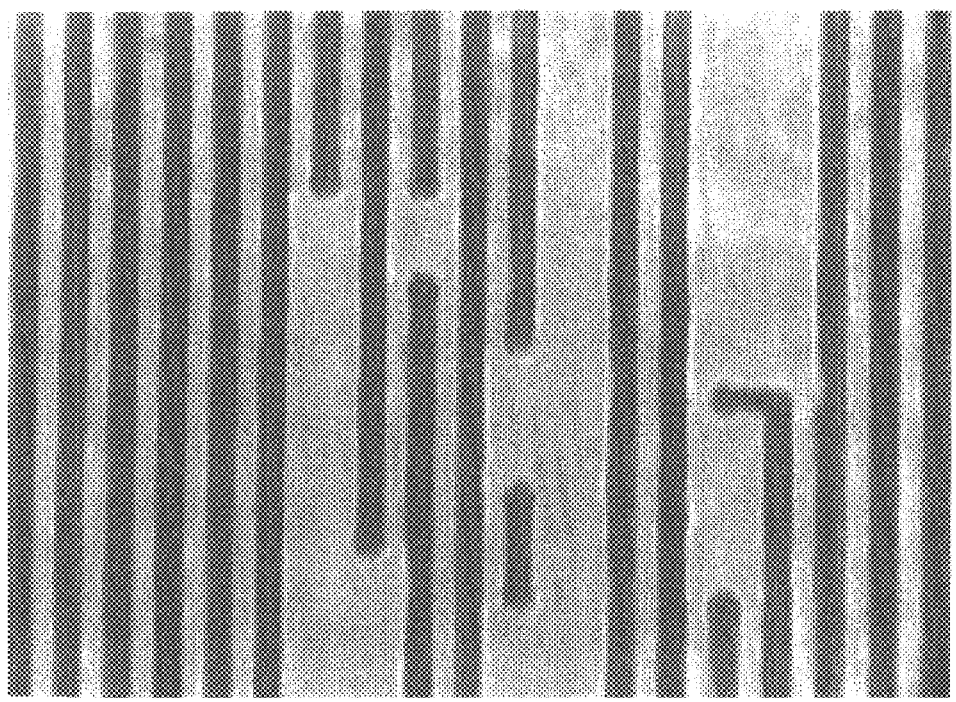
Figure 2B:
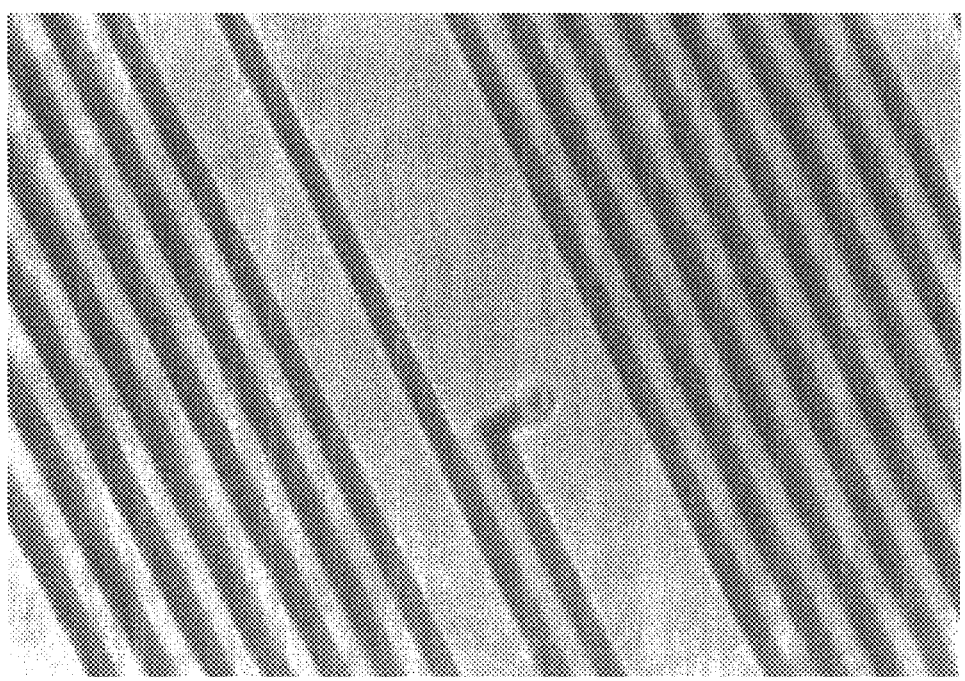

To insure even exposure throughout the thickness of the resist, it must be relatively transparent at the exposure frequency, which is usually in the ultraviolet region of the spectrum as hereinafter detailed. To enable verification of alignment to features below, however, the resist must be relatively transparent in the visible range of the spectrum, which makes it extremely difficult visually to inspect for defects. This invention, however, enables the resist to be inspected, either manually or automatically or semi-automatically, by eliminating the image of the underlying layer(s). This is achieved by fluorescing the resist as shown in FIGS. 1B and 2B. FIGS. 1B and 2B show the effect of fluorescing the respective resists of FIGS. 1A and 2A, with the bright (fluorescent light) portions being the fluorescing resist portions. This can be achieved by adding a fluorescent material to the resist in the event that the resist does not already fluoresce naturally. FIGS. 1A,B and 2A,B were obtained using commercially available polyimid resists produced by Shipley Corporation, which were found to emit fluorescent light in about the 600–700 nm wavelength range when excited by laser light in about 488–514 nm wavelength range.

Figure 3A:
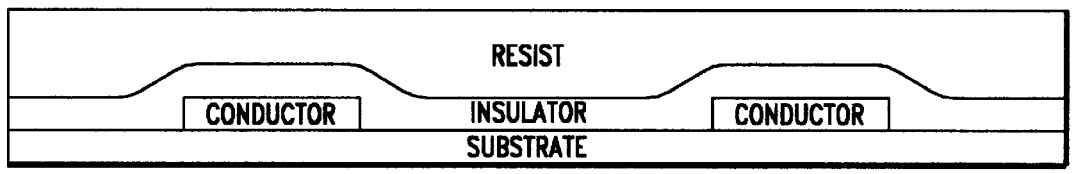
Figure 3B:
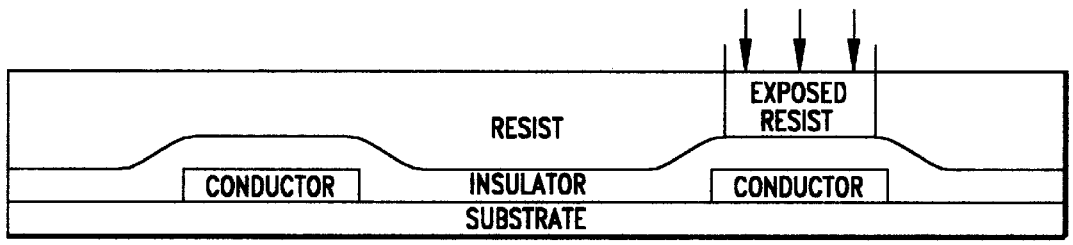
Figure 3C:
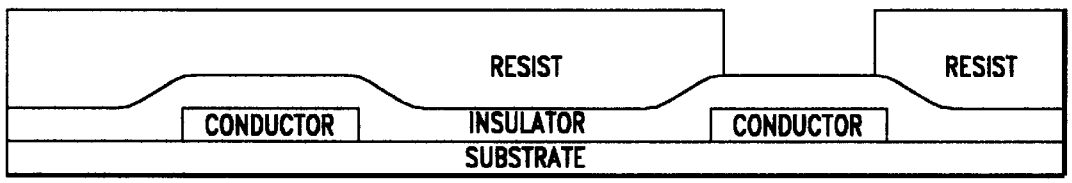
Figure 3D:
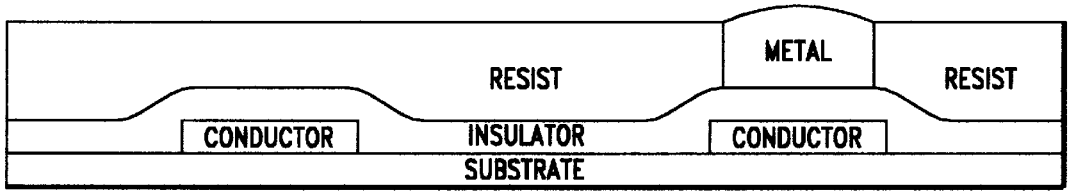
Figure 3E:
Figure 4A:
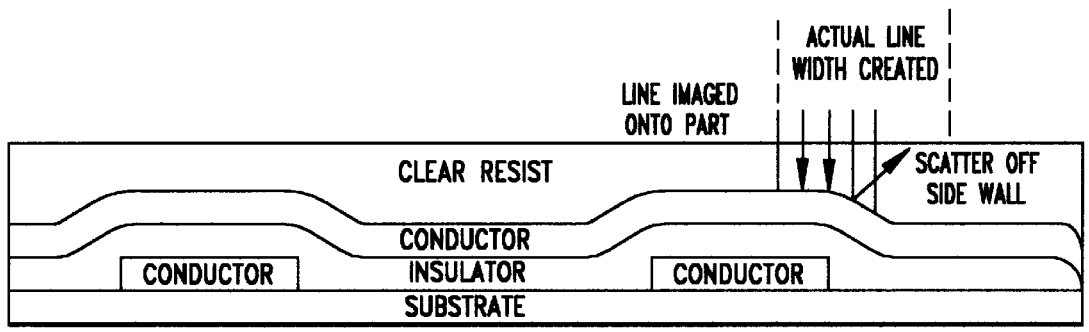
Figure 4B:
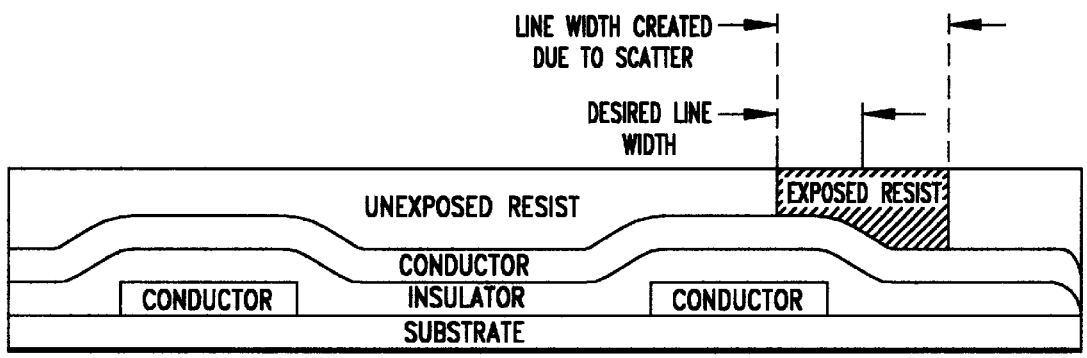
Figure 5A:
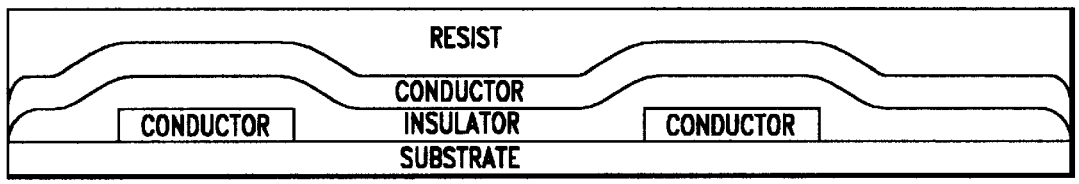
Figure 5B:
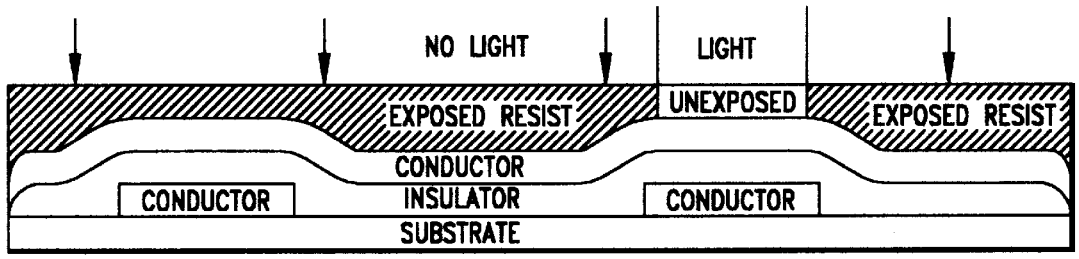
Figure 5C:
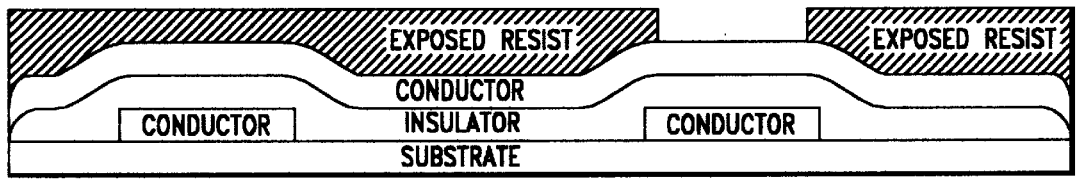
Figure 5D:
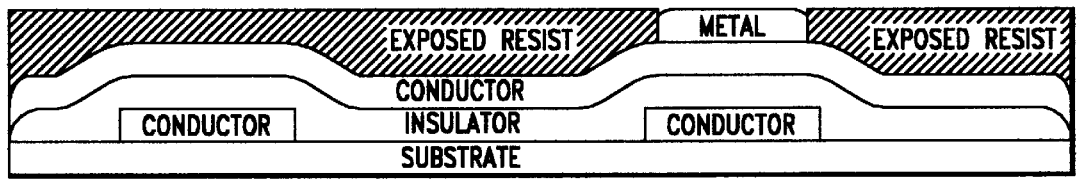
Figure 5E:
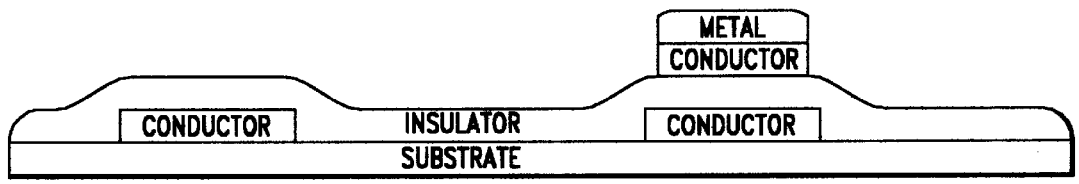

To fabricate a circuit using either resist type, a pattern of conductors is laid on a substrate and covered with a layer of insulator which may in turn be covered by a layer of conducting material, all followed by a layer of photoresist (FIGS. 3a, 4a and 5a). The photoresist, a fluid material, fills in the uneven surface beneath it, and its top surface remains flat. Positive resist becomes soluble where light hits it, and negative resist becomes insoluble where light hits it. That is, after soluble resist is removed, positive resist reveals metal where light hit the resist, and negative resist shows metal where the resist was not exposed to light.

Manufacturing processes, as previously stated, can be additive or subtractive. In a subtractive process, bare conductor is etched away, while insoluble resist protects the layer where the conductor is desired. In an additive process, no second conductor layer is applied to the part; and removing soluble resist, reveals areas where the conductor is desired and metal is applied, forming the intended conductor pattern. Regardless of the type of fabrication process, resists are transparent under white light (FIGS. 1A,2A) and can be made to appear visible under appropriate fluorescing—exciting light (FIGS. 1B, 2B).

FIG. 3 shows an example of a positive additive process, and FIG. 4 shows a negative subtractive process. In the positive additive process, the resist is exposed to light along the desired conducting pattern (FIG. 3b). The exposed resist becomes soluble and washes away, revealing the insulating layer underneath (FIG. 3c). A layer of metal is deposited on the part, adhering to the bare conducting layer (FIG. 3d). The unexposed resist is removed, along with the metal above it, leaving a conductor adhered to the insulating layer (FIG.

Figure 4C:
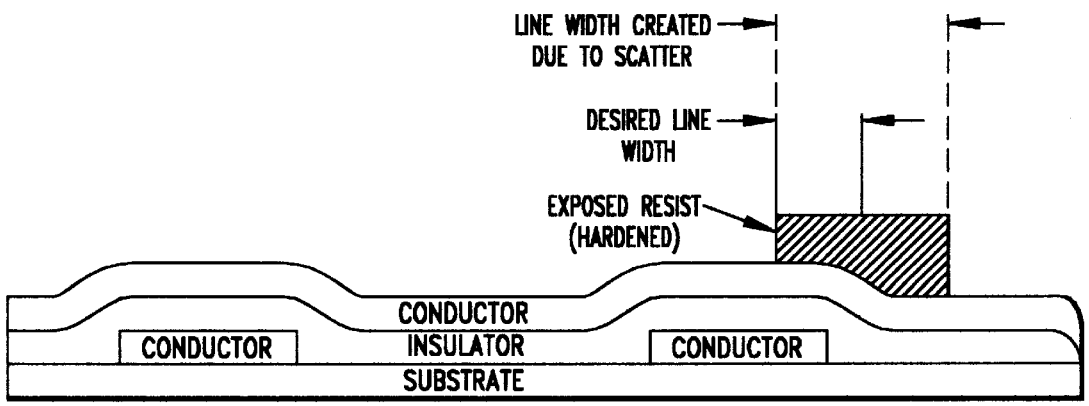
Figure 4D:
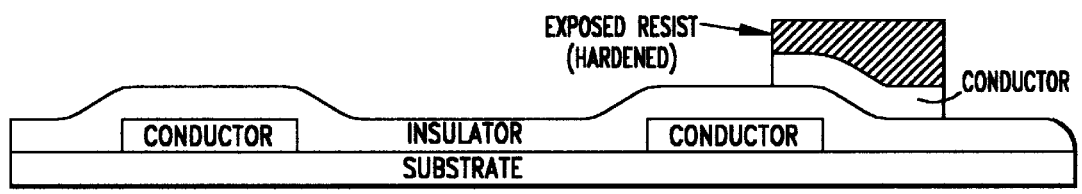
Figure 4E:
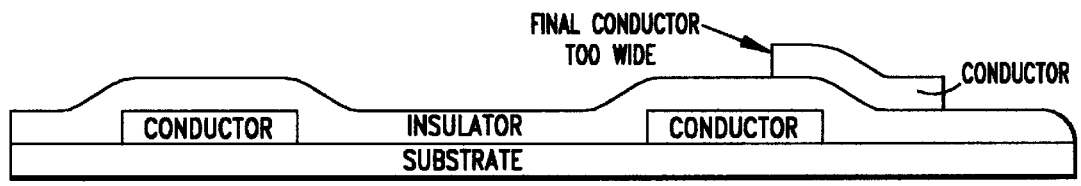

3e). In the exemplary negative subtractive process of FIG. 4b, the photoresist is exposed only along the desired conducting pattern. The unexposed resist is removed, leaving the conducting pattern covered with a layer of hardened photoresist (FIG. 4c). The bare conductor is etched away (FIG. 4d), and finally the hardened resist is removed as well (FIG. 4e).

FIG. 5 illustrates the use of a positive resist in combination with additive and subtractive processes. The resist is deposited on a thin layer of metal and the resist is removed where final metal is desired. A thicker layer of metal is deposited on top of the bare thin metal, which acts as a seed layer for bonding purposes. The remaining resist and thin metal below is etched away, leaving a thicker metal, only slightly reduced in height, still remaining.

In all of the above-stated processes, in actual practice, the conducting layer immediately below the resist is frequently an uneven surface, as schematically illustrated in FIG. 4. The light needed to expose the photoresist can reflect from the metal back through the resist, exposing a line wider than desired. For the purpose of absorbing light and reducing reflection from the underlying metal, dyes have accordingly been added to the transparent photoresists; but the increase in visibility is negligible for visual inspection because the resist must maintain its transparency to enable verification of alignment.

The Underlying Problem

Automated inspection of the fluorescent pattern, with underlying structures, has not heretofore been commercially possible because the returned fluorescent signal is weak, generally much too dim for rapid inspection, which requires much stronger signal because high speed scanning allows only a very short camera exposure time.

Underlying the present invention, is the discovery of techniques for materially increasing the available fluorescent light intensity, while suppressing reflections from lower surfaces or layers in the wafer or the like, now enabling practical high speed automated fluorescence inspection through such increased efficiency of the signal and by using a more sensitive scanning technique and device.

As explained in my said co-pending application, the fluorescent light rays from each point of the fluorescing surfaces are emitted in all directions, and rays can be collimated for the imaging camera that are not just in the vertical incident excitation light ray direction. Some fluorescent light rays will travel back to the camera from all of flat, angled, and irregular and bumpy portions of the surface and independent of the angle of the fluorescing surface or the angle of illumination, because each fluorescing particle emits lights in all spherical (semi-) directions. The use of the fluorescence thus is not just to obtain contrast, but also to create some emitted rays independent of the angle of incidence of the excitation onto the surface being inspected, enabling the imaging of all curved surfaces and non-planar surfaces, as well. Such would not be imaged or seen with normal reflected or scattered light, but only with imaging fluorescent light. As further explained in my co-pending application and in said patent to Yamanaka, an appropriate filter in front of the imaging camera permits only imaging of the fluorescent rays, blocking out all other light.

Since the underlying purpose of the present invention is automatically to inspect wafers, circuit boards, chip modules and the like, for pattern defects at high scanning speeds, appropriate sources of illumination and of imaging detectors must be considered. Conventional television cameras, for example, are not suitable because images moving at high speeds create a blur. Photomultiplier tubes, which only look at a single point, are too slow for inspection. Very high sensitivity is required, moreover, since usable laser power is restricted and, in some cases, extreme care is necessary not to overexcite the material or to burn it. The decision was accordingly reached to use a time-delay-integration (TDI) charge-coupled device (CCD) so as to enable scan at high speeds without obtaining blur.

To obtain efficient illumination, at least three sources for possible use for fluorescing were studied: Mercury lamps, xenon lamps, and lasers. Mercury lamps, however, were determined to produce only small amounts of fluorescent-exiting energy in resin materials; for example, for 488 nanometers, typically in the order of 5 milliwatts. Xenon lamps are only slightly better, producing only 20 milliwatts. In accordance with a preferred version of the present invention, an air-cooled argon laser has been found to be most useful, producing 1000 milliwatts. It is further important to place the excitation frequency where the camera is looking, and, again, efficiently to use all available power. For the linear time-delay-and-integrated CCD, a rectangle is viewed by the charge-coupled device, so that illumination of a rectangle is required. Slit illumination by a laser was accordingly chosen to fluoresce the photoresist, produced with a cylindrical lens as shown in FIG. 6. Such has been discovered to yield the most efficient use of the available power, as all the light from the laser is focused into the scanning region. To do this, a beam expander lens 1 is employed, FIG. 6, to create a beam of diameter preferably corresponding to the long dimension of the rectangle, followed by an external cylindrical lens 3 to collapse the circle into a slit of appropriate length. This way, all power of the laser is placed exactly where the system is looking.

While in the systems of said copending application and said patent, the laser source directs its beam upon an inclined mirror to reflect the beam vertically downward upon the wafer surface, and receives at the imaging camera the excited fluorescent rays vertically upward, it has been found that impinging the excitation beam at an angle to the surface (and to the vertical) increases the fluorescent spherical emission available at the camera and from all surface portions, including irregularities and surface bumps. Preferably, indeed, a pair of laser sources directing incident beams from opposites sides and at such inclined angles are used as shown in later-discussed FIG. 7.

Because the fast scanning in high speed inspection provides very little time to collect light and hence requires a strong excitation source such as multiple lasers, the mere use of such to increase power normally runs into the problem that coherent beams will interfere and cancel one another. If two separate lasers or laser paths are so used, the beams will not be phase locked and the interference pattern can well be time varying. While certain phase randomizing devices are available, the cost in reducing power with such, would undo the benefit of using multiple beams. With the technique of the present invention, however, employing time-delay-and-integrate CCD cameras with the pair of oppositely inclined beams, the beams may effectively add without the loss of power.

Considering, then, the multiple laser illumination system of FIG. 7, a pair of lasers on opposite sides of the imaging camera TDI-CCD directs respective beams through beam expanders 1 and 1' (as in FIG. 6) upon mirrors that direct the expanded circular beams through cylindrical lenses 3 and 3' to generate slits of light 5 and 5' impinging at similar but opposite inclined angles (preferably about 45°) upon the resist-conductor surface (schematically represented as "r", "p" in FIG. 7), of the wafer on the scanning stage, so labeled.

By using the time delay integration CCD camera (TDI-CCD) of pixel-reviewing horizontal sensor rows 1–n (A,B, C,D, etc.) and vertical columns 1–n, the fluorescent rays emitted from the laser-beam excited wafer surface and collimated at the camera produce pixels at the camera ($P_A$, etc.) summed over each column, with the output of the CCD being the sum power of both beams. This result is attained in accordance with the invention by causing the integrated charge in the time-delay-andintegrate CCD to be electrically moved at the same speed in the device as the wafer surface is moved on the scanning stage or is otherwise scanned. Each time the stage moves one row, the charge is shifted one row on the device. Each laser beam slit ($5,5^1$) is therefore positioned to enable illumination of a different group of rows along the CCD, such that the total power output is the sum of each group of rows being illuminated from each laser-beam fluorescent excitation of the wafer surface. Since, for example, the output with 100 units of light on one row produces the same output as a time-delay-ingintegrated CCD with one unit of light on each of 100 rows, the positioning of each beam signal distribution will not be overlapping, as shown in FIG. 9, producing the net effect of the sum of the fluorescent signals stimulated by each laser independently. Since the width of each beam can be easily focused, multiple laser beam power can thus be added together in this way, without exact frequency coherence, in accordance with the invention, enabling an extremely efficient fluorescent excitation system. The use of the very sensitive time-delay-and-integrate camera system, further enables the imaging of fluorescing surfaces also with great efficiency. The filtering out of all but the fluorescent rays, at the camera, FIG. 7, moreover, blocks out or masks all reflections from lower layers in the wafer or other device, and, as shown in FIGS. 1B and 2B; enables selective viewing of conductors on the fluorescing surface.

While the use of a pair of oppositely inclinedly directed slit beams of laser light from a pair of different but similar lasers is shown in FIG. 7, the two slit beams may, if desired, be derived from a single common laser source as shown in FIG. 10, using a beam splitter to create two paths, and adjusting the operation of the paths (length or other variations) to avoid exact frequency coherency that might otherwise generate frequency beats with cancellation effects, as before described. In either case (FIGS. 7 or 10), the light-opaque conductor line pattern "p" on the top fluorescent resist layer "r" of a multi-layer integrated circuit wafer or circuit board or the like, are optically inspected to the exclusion of patterns on lower layers, by directing the fluorescent-excitation laser light of a predetermined frequency(ies) upon said layer along a pair of beams impinged as slits 5,5' from opposite sides of the layer at opposite inclined angles thereto. The optical inspecting of the fluorescent light of different fluorescing frequency from the top layer in response to the directing of the pair of beams thereupon, creates an illuminated top layer fluorescing light background masking the lower layers, and upon which the conductor line pattern appears as dark lines, (FIGS. 1B and 2B). The operation of the pair of laser beams is adjusted or is such as to avoid exact frequency coherency that might, as before noted, generate frequency beats; and said opposite inclined angles of the pair of beams are adjusted to eliminate the possible generation of dark shadow zones between proximal edges of adjacent conductor lines between the lines as shown in FIGS. 1B and 2B, and that might otherwise be misinterpreted as a dark conductor line. The inspecting is effected by monitoring the fluorescing light in the TDI CCD along successive rows of pixel sensors thereof as the top layer is scanned, and wherein the resulting integrated charge in the CCD is electrically shifted at the same speed as such scanning; and positioning each laser beam to illuminate a different group of rows along the CCD, to produce a net effect of summing the monitored fluorescent light signals produced by each laser beam independently.

The slit laser beams are preferably formed, as before described, by first expanding the original beam into a substantially circular beam and then passing the expanded beam through a cylindrical lens to flatten the beam to serve as a slit of laser light for impinging upon said top layer.

The results of the previously described FIGS. 1B and 2B were obtained with an argon laser emitting 488 nm and 514 nm frequency illumination (model Las-1000, produced by Laser Physics) The system also used a TDI (Time Delay Integration) CCD camera chip for scanning (model 1024×96 TDI by Reticon) The pair of oppositely side-directed laser beam slits were inclined at an angle of about 45° to the vertical and to the plane of the wafer surface.

In some applications, however, small line breaks and the like may not be illuminated where the pair of inclined beams casts shadows over the break from the side edges thereof For such situations, it has been found that adjusting one of the inclined beams up to an angle of 90° or so, as shown with the left-hand laser beam directed at substantially normal incidence N to the wafer in FIG. 11, and with the other (right-hand) beam still at an acute angle, such problems may be admirably solved.

As before stated, furthermore, the fluorescent resist inspection process of the invention also lends itself to the incorporation of other automatic inspection features outlined in the system block diagram of FIG. 12, wherein a laser-simulated fluorescent resist imaging system (which may also be that of FIG. 7 and 10) is shown cooperating with several imaging cameras—a color camera for TV monitor display (so-labeled), and top and bottom cameras for the wafer or other device inspection stage. The last-named cameras may allow comparison for A/D and material identification, in turn with well-known pattern reference and design rule analysis. The scanning stage may be automatically computer controlled and monitored, as shown, with detected defect information fed to the computer from a defect collection buffer.

Further modifications and applications and uses of the invention and its methodology will also occur to those skilled in this art, and such are considered to fall within the spirit and scope of the invention as defined in the appended claims.

What is claimed is:

1. A method of optically inspecting the light-opaque conductor line pattern on the top layer of a multi-layer integrated circuit wafer or element to the exclusion of patterns on lower layers, that comprises, forming the conductor line pattern on such a top layer of a material that fluoresces in response to laser light of predetermined frequency(ies) and wherein the fluorescing frequency is different from the predetermined frequency, directing laser light of said predetermined frequency(ies) upon said layer along a pair of beams impinged from opposite sides of the layer at opposite inclined angles thereto; optically inspecting the light of said different frequency fluorescing from the top layer in response to directing of the pair of beams thereupon, creating an illuminated top layer fluorescing light background masking the lower layers and upon which the conductor line pattern appears as dark lines; adjusting the operation of the pair of laser beams to avoid exact frequency coherency that might generate frequency beats; and adjusting said opposite inclined angles of the pair of beams to eliminate the generation of dark shadow zones between proximal edges of adjacent conductor lines between the lines that might otherwise be misinterpreted as a dark conductor line.

2. The method claimed in claim 1 wherein increased beam power is achieved by generating said pair of beams from a pair of separate lasers.

3. The method claimed in claim 1 wherein the pair of beams is produced by optically splitting a common laser beam to create the pair of beams.

4. The method claimed in claim 1 wherein the inspecting is effected by monitoring the fluorescing light in a time-delay-integration CCD along successive rows of pixel sensors thereof as the top layer is scanned, and wherein the resulting integrated charge in the CCD is electrically shifted at the same speed as such scanning, and positioning each laser beam to illuminate a different group of rows along the CCD, to produce a net effect of summing the monitored fluorescent light signals produced by each laser beam independently.

5. The method claimed in claim 1 wherein each laser beam is first expanded in a substantially circular beam and then is passed through a cylindrical lens to flatten the beam to serve as a slit of laser light for impinging upon said top layer.

6. Apparatus for optically inspecting the light-opaque conductor line pattern on the top layer of a multi-layer integrated circuit wafer or element to the exclusion of patterns on lower layers, wherein the conductor line pattern is formed on such a top layer of a material that fluoresces in response to laser light of predetermined frequency(ies) and wherein the fluorescing frequency is different from the predetermined frequency, said apparatus having, in combination, means for generating and directing laser light of said predetermined frequency(ies) upon said top layer along a pair of beams impinged from opposite sides of the layer at opposite inclined angles thereto; means for optically inspecting the light of said different frequency fluorescing from the top layer in response to the directing of the pair of beams thereupon, creating an illuminated top layer fluorescing light background masking the lower layers and upon which the conductor line pattern appears as dark lines, means for adjusting the operation of the pair of laser beams to avoid exact frequency coherency that might generate frequency beats; and means for adjusting said opposite inclined angles of the pair of beams to eliminate the generation of dark shadow zones between proximal edges of adjacent conductor lines between the lines that might otherwise be misinterpreted as a dark conductor line.

7. The apparatus claimed in claim 6 wherein increased beam power is achieved by means for generating said pair of beams from a pair of separate lasers.

8. The apparatus as claimed in claim 6 wherein the pair of beams is produced by means for optically splitting a common laser beam to create the pair of beams.

9. The apparatus claimed in claim 6 wherein the inspecting is effected by means for monitoring the fluorescing light in a time-delay-integration CCD having successive rows of pixel sensors; means for scanning said rows as the top layer is scanned at a predetermined speed; means for electrically shifting the resulting integrated charge in the CCD at the same speed as such scanning; and means for positioning each laser beam to illuminate a different group of rows along the CCD, to produce a net effect of summing the monitored fluorescent light signals produced by each laser beam independently.

10. The apparatus claimed in claim 6 wherein each laser beam is first expanded by a beam-expanding lens in a substantially circular beam and then is passed through a cylindrical lens to flatten the beam to serve as a slit of laser light for impinging upon said top layer.

11. A method of optically inspecting the light-opaque conductor line pattern on the top layer of a multi-layer integrated circuit wafer or element to the exclusion of patterns on lower layers, that comprises, forming the conductor line pattern on such a top layer of a material that fluoresces in response to laser light of predetermined frequency(ies) and wherein the fluorescing frequency is different from the predetermined frequency, directing laser light of said predetermined frequency(ies) upon said layer at an inclined angle thereto; optically inspecting the light of said different frequency fluorescing from the top layer in response to directing of the laser light thereupon, creating an illuminated top layer fluorescing light background masking lower layers and upon which background the conductor line pattern appears as dark lines; and adjusting said inclined angle to minimize the generation of dark shadow zones between proximal edges of adjacent conductor lines between the lines that might otherwise be misinterpreted as a dark conductor line.

12. The method claimed in claim 11 wherein the laser light is first expanded in a substantially circular beam and then is flattened to serve as a slit of laser light for impinging at said inclined angle upon said top layer.

13. The method as claimed in claim 11 wherein the inspecting is effected by monitoring the fluorescing light in a time-delay-integration CCD along successive rows of pixel sensors thereof as the top layer is scanned, and wherein the resulting integrated charge in the CCD is electrically shifted at the same speed as such scanning.

14. The method claimed in claim 11 wherein said material is a resist, transparent to visible light and activatable by laser light in about 488–514 nm wavelength range to emit visible light in about the 600–700 nm wavelength range.

15. Apparatus for optically inspecting the light-opaque conductor line pattern on the top layer of a multi-layer integrated circuit wafer or element to the exclusion of patterns on lower layers, wherein the conductor line pattern is formed on such a top layer of a resist material that fluoresces in response to laser light of predetermined frequency(ies) and wherein the fluorescing frequency is different from the predetermined frequency, said apparatus having, in combination, means for generating and directing laser light of said predetermined frequency(ies) upon said top layer along a beam impinged at an inclined angle thereto; means for optically inspecting the light of said different frequency fluorescing from the top layer in response to directing of the beam thereupon, creating an illuminated top layer fluorescing light background masking lower layers and upon which the conductor line pattern appears as dark lines; and means for adjusting said inclined angle of the beam to minimize the generation of dark shadow zones between proximal edges of adjacent conductor lines between the lines that might otherwise be misinterpreted as a dark conductor line.

16. The apparatus in claim 15 wherein the inspecting is effected by means for monitoring the fluorescing light in a time-delay-integration CCD having successive rows of pixel sensors; means from scanning said rows as the top layer is scanned at a predetermined speed; and means for electrically shifting the resulting integrated charge in the TDI CCD at the same speed as such scanning.

17. The apparatus claimed in claim 15 wherein the laser beam is first expanded by a beam-expanding lens in a substantially circular beam and then is passed through a cylindrical lens to flatten the beam to serve as a slit of laser light for impinging at said inclined angle upon said top layer.

18. The apparatus of claim 15 wherein said inclined angle is about 45 degrees.

19. The apparatus claimed in claim 15 wherein means is provided for directing a further laser beam to impinge substantially normal to said top layer.

20. The method claimed in claim 11 wherein a further laser beam is impinged substantially normal to said top layer.

* * * * *